United States Patent
Shen et al.

(10) Patent No.: US 11,015,212 B2
(45) Date of Patent: May 25, 2021

(54) METHODS OF REDUCING FOAM DURING ETHANOL FERMENTATION

(71) Applicant: NOVOZYMES A/S, Bagsvaerd (DK)

(72) Inventors: Xinyu Shen, Wake Forest, NC (US); Kim Borch, Birkerød (DK); Justin Schroeder, Iowa City, IA (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 16/342,249

(22) PCT Filed: Oct. 17, 2017

(86) PCT No.: PCT/US2017/056852
§ 371 (c)(1),
(2) Date: Apr. 16, 2019

(87) PCT Pub. No.: WO2018/075430
PCT Pub. Date: Apr. 26, 2018

(65) Prior Publication Data
US 2019/0249203 A1 Aug. 15, 2019

Related U.S. Application Data

(60) Provisional application No. 62/409,169, filed on Oct. 17, 2016.

(51) Int. Cl.
*C12P 7/14* (2006.01)
*C12P 7/06* (2006.01)
*C12N 9/18* (2006.01)
*C12N 9/48* (2006.01)
*C12N 9/16* (2006.01)
*C12N 9/24* (2006.01)
*C12N 9/28* (2006.01)

(52) U.S. Cl.
CPC .............. *C12P 7/14* (2013.01); *C12N 9/16* (2013.01); *C12N 9/18* (2013.01); *C12N 9/2417* (2013.01); *C12N 9/48* (2013.01); *C12P 7/06* (2013.01); *C12Y 301/01004* (2013.01); *C12Y 301/04003* (2013.01); *C12Y 302/01001* (2013.01); *Y02E 50/10* (2013.01)

(58) Field of Classification Search
CPC ................................ C12P 7/06; C12N 9/18
See application file for complete search history.

(56) References Cited

U.S. PATENT DOCUMENTS 10,144,919 B2 * 12/2018 Xu .................. C12N 9/16
2017/0096619 A1 * 4/2017 Segura ............. C11B 3/003

FOREIGN PATENT DOCUMENTS

| WO | 2008/135547 A1 | 11/2008 |
|---|---|---|
| WO | 2012/122613 A1 | 9/2012 |
| WO | 2014/147219 A1 | 9/2014 |
| WO | 2014/205198 A1 | 12/2014 |
| WO | 2015/140275 A1 | 9/2015 |

OTHER PUBLICATIONS

Ganidi et al, 2009, Bioresource Technology 100(23), 5546-5554.

* cited by examiner

*Primary Examiner* — Suzanne M Noakes
(74) *Attorney, Agent, or Firm* — David Fazzolare

(57) ABSTRACT

The invention relates to methods of reducing foam during ethanol fermentation by adding a phospholipase A and/or a phospholipase C during fermentation.

22 Claims, 1 Drawing Sheet
Specification includes a Sequence Listing.

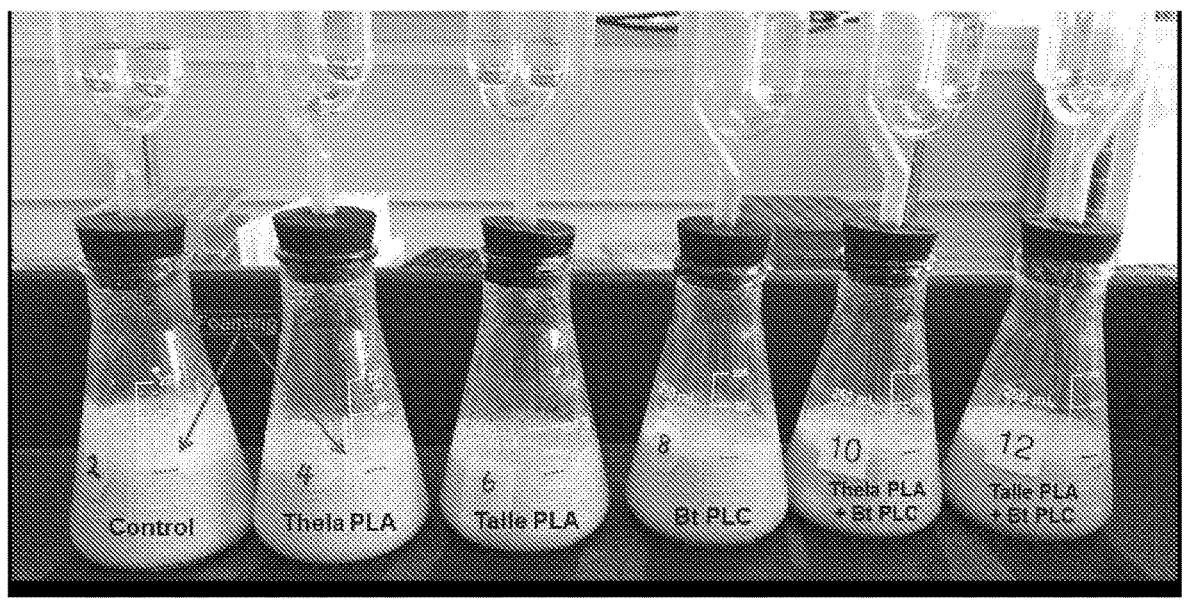

METHODS OF REDUCING FOAM DURING ETHANOL FERMENTATION

CROSS-REFERENCE TO RELATED APPLICATIONS

This application is a 35 U.S.C. 371 national application of international application no. PCT/US2017/056852 filed Oct. 17, 2017, which claims priority or the benefit under 35 U.S.C. 119 of U.S. application No. 62/409,169 filed Oct. 17, 2016, the contents of which are fully incorporated herein by reference.

FIELD OF THE INVENTION

The present invention relates to methods of reducing foam during ethanol fermentation and processes of producing ethanol including a fermentation step defoamed using a method of the invention.

BACKGROUND OF THE INVENTION

Ethanol for use as fuel is typically produced by first grinding starch-containing material in a dry-grind or wet-milling process, then degrading the material into fermentable sugars using enzymes and finally converting the sugars directly or indirectly into the desired fermentation product using a fermenting organism. The ethanol may be recovered from the fermented mash (often referred to as "beer mash"), e.g., by distillation, which separate the ethanol from other liquids and/or solids.

WO 2008/135547 concerns reducing foam in processes for production of a fermentation product by contacting the fermentation media comprising a fermenting organism with a lipolytic enzyme selected from the group consisting of phospholipase, lyso-phospholipase and lipase, and a metal salt.

WO 2014/147219 concerns a phospholipase A from *Talaromyces leycettanus*.

WO2015/140275 discloses a phospholipase C from *Bacillus thuringiensis*.

Foam generation during ethanol fermentation is a major problem, especially in ethanol production processes where starch-containing material is liquefied with an alpha-amylase and a protease before saccharification and fermentation.

Therefore, there is a desire to reduce foam in ethanol fermentation.

SUMMARY OF THE INVENTION

The object of the present invention is to provide methods of reducing foam in a fermentation medium during ethanol fermentation where fermentable sugars are converted into ethanol by a fermenting organism, such as yeast. The invention also relates to processes of producing ethanol from starch-containing material using a defoming method of the invention.

The inventor have surprisingly found that when adding phospholipase A from *Talaromyces leycettanus* (SEQ ID NO: 2) and/or phospholipase C from *Bacillus thuringiensis* (SEQ ID NO: 7) foam generated before and/or during ethanol fermentation can be reduced or prevented. Foam is especially a problem when the ethanol fermentation is carried out using yeast in a fermentation medium comprising fermentable sugars derived from starch-containing material which has been liquefied in the presence of an alpha-amylase and a protease before saccharification and ethanol fermentation.

Therefore, in the first aspect the invention relates to methods of reducing foam during ethanol fermentation, wherein a phospholipase A and/or phospholipase C is present and/or added during fermentation.

In an embodiment the phospholipase(s) is(are) added to the yeast propagation tank.

In a preferred embodiment the phospholipase A is the mature part of the sequence shown as SEQ ID NO: 2 or a sequence having a sequence identity thereto of at least 60%, at least 65%, at least 70%, at least 75%, at least 80%, at least 85%, at least 90%, at least 95%, at least 96%, at least 97%, at least 98%, at least 99%.

In an embodiment the phospholipase A is derived from a strain of *Talaromyces*, in particular *Talaromyces leycettanus*. The phospholipase A may be a phospholipase A1 classified under E.C. 3.1.1.32.

In a preferred embodiment the phospholipase C is the mature part of the sequence shown as SEQ ID NO: 7, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

In an embodiment the phospholipase C is derived from a strain of *Bacillus*, in particular *Bacillus thuringiensis*. The phospholipase C may be one classified under E.C. 3.1.4.3.

In an embodiment the phospholipase A shown in SEQ ID NO: 2 and phospholipase C shown in SEQ ID NO: 7 may be present and/or added during fermentation.

In another aspect the invention relates to processes of producing ethanol, comprising (a) converting a starch-containing material into dextrins with an alpha-amylase;

(b) saccharifying the dextrins using a carbohydrate-source generating enzyme, in particular a glucoamylase, to form fermentable sugars;

(c) fermenting the fermentable sugars into ethanol using a fermenting organism; wherein phospholipase A and/or phospholipase C is(are) present and/or added during steps (b) and/or (c).

In a preferred embodiment the phospholipase A, e.g., one derived from a strain of *Talaromyces*, in particular *Talaromyces leycettanus*, is the mature part of the sequence shown as SEQ ID NO: 2, or one having a sequence identity thereto of at least 60%, at least 65%, at least 70%, at least 75%, at least 80%, at least 85%, at least 90%, at least 95%, at least 96%, at least 97%, at least 98%, at least 99%.

In a preferred embodiment the phospholipase C is the mature part of the sequence shown as SEQ ID NO: 7, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

In an embodiment the phospholipase C is derived from a strain of *Bacillus*, in particular *Bacillus thuringiensis*, In an embodiment the phospholipase A shown in SEQ ID NO: 2 and phospholipase C shown in SEQ ID NO: 7 may be present and/or added during fermentation.

In a preferred embodiment a protease is present and/or added during liquefaction step (a).

In a preferred embodiment the protease is a bacterial protease. In a preferred embodiment the protease is a serine protease, in particular one derived from *Pyrococcus*. Specifically contemplated is a *Pyrococcus furiosus* protease, such as the one shown as SEQ ID NO: 4 herein.
}

In one aspect the invention also relates to the use of a phospholipase A and/or a phospholipase C for defoaming ethanol fermentation. In an embodiment the phospholipase A is the mature part of the sequence shown as SEQ ID NO: 2, or one having a sequence identity thereto of at least 60%, at least 65%, at least 70%, at least 75%, at least 80%, at least 85%, at least 90%, at least 95%, at least 96%, at least 97%, at least 98%, at least 99%.

BRIEF DESCRIPTION OF THE DRAWING

FIG. 1 shows foaming after 7 hours of SSF using glucoamylase with and without phospholipase A and/or C on corn mash liquefied with alpha-amylase and protease.

DETAILED DESCRIPTION OF THE INVENTION

The object of the present invention is to provide methods of reducing foam in a fermentation medium during ethanol fermentation where fermentable sugars are converted into ethanol by a fermenting organism, such as yeast. The invention also relates to processes of producing ethanol from starch-containing material using a defoaming method of the invention.

Methods of Reducing Foam During Ethanol Fermentations

In the first aspect the invention relates to methods of reducing foaming during ethanol fermentation, wherein a phospholipase A and/or a phospholipase C is(are) present and/or added during fermentation.

In a preferred embodiment the phospholipase A, e.g., one derived from a strain of *Talaromyces*, in particular *Talaromyces leycettanus*, is the mature part of the sequence shown as SEQ ID NO: 2, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

In a preferred embodiment the phospholipase C, e.g., one derived from a strain of *Bacillus*, in particular *Bacillus thuringiensis*, is the mature part of the sequence shown as SEQ ID NO: 7, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

In an embodiment the phospholipase A shown in SEQ ID NO: 2 and the phospholipase C shown as SEQ ID NO: 7 are present and/or added during fermentation.

The fermentation is carried in a fermentation medium comprising a fermenting organism, in particular yeast, and fermentable sugars. The fermentable sugars may be derived by saccharifying starch-containing material with a carbohydrate-source generating enzyme, in particular a glucoamylase, and optionally an alpha-amylase, e.g., an acid fungal alpha-amylase.

According to the invention the phospholipase A and/or phospholipase C may be present or added during ethanol fermentation carried out in a fermentation medium comprising fermentable sugars derived from starch-containing material liquefied with an alpha-amylase and optionally a protease. In a preferred embodiment the phospholipase A and/or phospholipase C is(are) present and/or added during fermentation carried out in a fermentation medium comprising fermentable sugars derived from starch-containing material first liquefied with an alpha-amylase and a protease and then saccharified with a carbohydrate-source generating enzyme, in particular a glucoamylase, and optionally an acid fungal alpha-amylase.

Examples of suitable and preferred enzyme can be found below.

Process of Producing Ethanol According to the Invention

In another aspect the invention relates to processes of producing ethanol, comprising (a) converting a starch-containing material into dextrins with an alpha-amylase;

(b) saccharifying the dextrins using a carbohydrate-source generating enzyme, to form fermentable sugars;

(c) fermenting the fermentable sugars into ethanol using a fermenting organism; wherein phospholipase A and/or phospholipase C is(are) present and/or added during steps (b) and/or (c).

Generally the starch-containing material in step (a) may contain 20-55 wt.-% dry solids (DS), preferably 25-40 wt.-% dry solids, more preferably 30-35% dry solids.

In a preferred embodiment step (a) is a liquefaction step carried out at a temperature above the initial gelatinization temperature.

In a preferred embodiment saccharification step (b) and fermentation step (c) are carried out simultaneously (SSF).

In a preferred embodiment the phospholipase A used in accordance with the invention is derived from a strain of *Talaromyces*, in particular *Talaromyces leycettanus*. The mature part of the phospholipase A polypeptide sequence is shown as SEQ ID NO: 2. In an embodiment the phospholipase A has a sequence identity to SEQ ID NO: 2 of at least 60%, at least 65%, at least 70%, at least 75%, at least 80%, at least 85%, at least 90%, at least 95%, at least 96%, at least 97%, at least 98%, at least 99%.

The phospholipase A may be present and/or added during sequential or simultaneous saccharification and fermentation (SSF) (i.e., simultaneous steps (b) and/or (c)).

In a preferred embodiment the phospholipase C used according to the invention is derived from a strain of *Bacillus*, in particular *Bacillus thuringiensis*, is the mature part of the sequence shown as SEQ ID NO: 7, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

In an preferred embodiment the phospholipase A shown in SEQ ID NO: 2 and phospholipase C shown in SEQ ID NO: 7 are present and/or added during fermentation.

Liquefaction Step (a)

In an embodiment the pH in step (a) is between 4-7, preferably between pH 4.5-6.

Step (a) may be carried out at as a liquefaction step at a temperature above the initial gelatinization temperature.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S. and Lii. C, Starch/Starke, Vol. 44 (12) pp. 461-466 (1992).

In an embodiment step (a) is carried out at a temperature between 70 and 100° C., in particular between 80-90° C., such as around 85° C.

In an embodiment a jet-cooking step may be carried out before in step (a). Jet-cooking may be carried out at a temperature between 95-140° C. for about 1-15 minutes, preferably for about 3-10 minutes, especially around about 5 minutes.

In an embodiment a process of the invention further comprises, before step (a), and optional jet-cooking step, the steps of:

i) reducing the particle size of the starch-containing material, preferably by dry milling;

ii) forming a slurry comprising the starch-containing material and water.

Alpha-Amylase

The alpha-amylase used in step (a) may be any alpha-amylase, but is preferably a bacterial alpha-amylase. In a preferred embodiment the bacterial alpha-amylase is derived from the genus *Bacillus*. A preferred bacterial alpha-amylase may be derived from a strain of *Bacillus stearothermophilus*, and may be a variant of a *Bacillus stearothermophilus* alpha-amylase, such as the one shown as SEQ ID NO: 1. *Bacillus stearothermophilus* alpha-amylases are typically truncated naturally during production. In particular the alpha-amylase may be a truncated *Bacillus stearothermophilus* alpha-amylase having from 485-495 amino acids, such as one being around 491 amino acids long (SEQ ID NO: 1).

According to the process of the invention the *Bacillus stearothermophilus* alpha-amylase may be the one shown as SEQ ID NO: 1 or one having a sequence identity thereto of at least 60%, at least 70%, at least 80%, at least 90%, at least 95%, at least 96%, at least 97%, at least 98%, at least 99%.

In an embodiment the bacterial alpha-amylase may be selected from the group of *Bacillus stearothermophilus* alpha-amylase variants comprising a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181+G182 compared to the amino acid sequence of *Bacillus stearothermophilus* alpha-amylase set forth as SEQ ID NO: 3 disclosed in WO 99/19467 or SEQ ID NO: 1 herein or the deletion of amino acids R179+G180 using SEQ ID NO: 1 herein for numbering.

In a preferred embodiment the *Bacillus stearothermophilus* alpha-amylase variant comprises one of the following set of mutations:

R179*+G180*;
I181*+G182*;
I181*+G182*+N193F; preferably
I181*+G182*+N193F+E129V+K177L+R179E;
I181*+G182*+N193F+V59A+Q89R+E129V+K177L+
R179E+H208Y+K220P+N224L+Q254S;
I181*+G182*+N193F+V59A Q89R+E129V+K177L+
R179E+Q254S+M284V; and
I181*+G182*+N193F+E129V+K177L+R179E+K220P+
N224L+S242Q+Q254S (using SEQ ID NO: 1 for numbering).

In an embodiment the *Bacillus stearothermophilus* alpha-amylase variant has a sequence identity to SEQ ID NO: 1 of at least 60%, at least 70%, at least 80%, at least 90%, at least 95%, at least 96%, at least 97%, at least 98%, at least 99%, but less than 100%.

In an embodiment the *Bacillus stearothermophilus* alpha-amylase variant has from 1-12 mutations, such as 1, 2, 3, 4, 5, 6, 7, 8, 9, 10, 11, or 12 mutations, compared to the parent alpha-amylase, especially the alpha-amylase shown as SEQ ID NO: 1.

Commercially available bacterial alpha-amylase products and products containing alpha-amylases include TERMAMYL™ SC, LIQUOZYME™ SC, LIQUOZYME™ LpH, AVANTEC™, AVANTEC™ AMP, BAN (Novozymes A/S, Denmark) DEX-LO™, SPEZYME™ XTRA, SPEZYME™ AA, SPEZYME™ FRED-L, SPEZYME™ ALPHA, GC358™, SPEZYME™ RSL, SPEZYME™ HPA and SPEZYME™ DELTA AA (from DuPont, USA), FUELZYME™ (Verenium, USA).

A bacterial alpha-amylase may be added in step (a) in an amount well-known in the art.

In an embodiment the bacterial alpha-amylase, e.g., *Bacillus* alpha-amylase, such as especially *Bacillus stearothermophilus* alpha-amylase, or variant thereof, is dosed in liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS. In an embodiment the bacterial alpha-amylase, e.g., *Bacillus* alpha-amylase, such as especially *Bacillus stearothermophilus* alpha-amylases, or variant thereof, is dosed to liquefaction in a concentration of between 0.0001-1 mg EP(Enzyme Protein)/g DS, e.g., 0.0005-0.5 mg EP/g DS, such as 0.001-0.1 mg EP/g DS.

Protease

In a preferred embodiment a protease is present and/or added during step (a). As mentioned above step (a) is preferably carried out at a temperature above the initial gelatinization temperature, such as between 70 and 100° C., in particular between 80-90° C., such as around 85° C.

The protease may be of bacterial origin. In an embodiment the protease is a serine protease, in particular one derived from a strain of *Pyrococcus*. In a preferred embodiment the protease is derived from a strain of *Pyrococcus furiosus*. In a specifically preferred embodiment the protease is the one shown as SEQ ID NO: 4.

In an embodiment the protease used in step (a) (in combination with an alpha-amylase) may be the protease shown as SEQ ID NO: 4 herein or a protease having at least 60%, such as at least 70%, such as at least 80%, such as at least 85%, such as at least 90%, such as at least 95%, such as at least 96%, such as at least 97%, such as at least 98%, such as at least 99% identity to SEQ ID NO: 4.

The *Pyrococcus furiosus* protease shown in SEQ ID NO: 4 herein is a thermostable bacterial protease. A commercial *Pyrococcus furiosus* protease product (Pfu S) from Takara Bio InC. (Japan) and is disclosed in U.S. Pat. No. 6,358,726 (hereby incorporated by reference). The thermostable *Pyrococcus furiosus* protease shown in SEQ ID NO: 4 is available from Novozymes A/S (Denmark) and has been found to have a thermostability value of 110% (80° C./70° C.) and 103% (90° C./70° C.) at pH 4.5 determined as described in Example 5 in WO 2013/082486 (hereby incorporated by reference).

In an embodiment the protease may, e.g., be derived from *Pyrococcus furiosus*, and may have the sequence shown as SEQ ID NO: 4 or may be a protease having at least 60%, at least 70%, at least 80%, at least 90%, at least 95%, at least 96%, at least 97%, at least 98%, or at least 99% sequence identity to SEQ ID NO: 4.

The protease, especially the *Pyrococcus furiosus* protease shown in SEQ ID NO: 4, may be added in step (a) in an amount of between 0.01 and 100 µg enzyme protein (EP)/g DS, such as levels between 0.10 and 10 µg EP/g DS, such as between 1 and 5 µg EP/g DS.

Saccharification Step (b)

Liquefaction step (a) is followed by saccharification of dextrins from step (b).

In an embodiment a process of the invention may comprise a pre-saccharification step, i.e., after step (a), but before saccharification step (b), carried out for 40-90 minutes at a temperature between 30-65° C.

According to the invention saccharification step (b) may be carried out at a temperature from 20-75° C., preferably from 40-70° C., such as around 60° C., and at a pH between 4 and 5.

In a preferred embodiment fermentation step (c) or simultaneous saccharification and fermentation (SSF) (i.e., combined steps (b) and (c)) may be carried out at a temperature between 20-60° C., preferably between 25-40° C., such as around 32° C. In an embodiment fermentation step (c) or simultaneous saccharification and fermentation (SSF) are ongoing for 6 to 120 hours, in particular 24 to 96 hours.

According to the invention a carbohydrate-source generating enzyme, preferably a glucoamylase, is present and/or added during saccharification step (b) and/or fermentation step (c) or simultaneous saccharification step (b) and fermentation step (c) (SSF).

The term "carbohydrate-source generating enzyme" includes any enzymes generating fermentable sugars. A carbohydrate-source generating enzyme is capable of producing one or more carbohydrates that can be used as an energy source by the fermenting organism(s) in question, for instance, when used in a process of the invention for producing ethanol. The generated carbohydrates may be converted directly or indirectly to the desired fermentation product, preferably ethanol. According to the invention a mixture of carbohydrate-source generating enzymes may be used.

Specific examples of carbohydrate-source generating enzyme activities include glucoamylase (being glucose generators), beta-amylase and maltogenic amylase (being maltose generators).

In a preferred embodiment the carbohydrate-source generating enzyme is a glucoamylase.

Glucoamylase Added During Saccharification and/or Fermentation (e.g., SSF)

The process of the invention, including steps (b) and/or (c), may be carried out using any suitable glucoamylase. The glucoamylase may be of any origin, in particular of fungal origin.

Contemplated glucoamylases include those from the group consisting of *Aspergillus* glucoamylases, in particular *A. niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (AgriC. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1 199-1204.

Other glucoamylases contemplated include glucoamylase derived from a strain of *Athelia*, preferably a strain of *Athelia rolfsii* (previously denoted *Corticium rolfsii*) glucoamylase (see U.S. Pat. No. 4,727,026 and (Nagasaka, Y. et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti*, *Talaromyces thermophilus* (U.S. Pat. No. 4,587,215). Also contemplated are *Trichoderma reesei* glucoamylases including the one disclosed as SEQ ID NO: 4 in WO 2006/060062 and glucoamylases being at least 80% or at least 90% identical thereto (hereby incorporated by reference).

In an embodiment the glucoamylase is derived from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*.

In an embodiments the glucoamylase present and/or added during saccharification step (b) and/or fermentation step (c) is of fungal origin, such as from a strain of *Pycnoporus*, or a strain of *Gloephyllum*. In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576 or SEQ ID NO: 6 herein.

In a preferred embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 5.

Other contemplated glucoamylases include glucoamylase derived from a strain of *Trametes*, preferably a strain of *Trametes cingulata* disclosed as SEQ ID NO: 34 in WO 2006/069289 (which is hereby incorporated by reference).

Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SANT™ SUPER, SANT™ EXTRA L, SPIRIZYME™ PLUS, SPIRIZYME™ FUEL, SPIRIZYME™ ULTRA, SPIRIZYME™ EXCEL, SPIRIZYME™ ACHIEVE, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.05-5 AGU/g DS (in whole stillage), especially between 0.1-2 AGU/g DS.

Glucoamylase may be added in an effective amount, preferably in the range from 0.001-1 mg enzyme protein per g DS, preferably 0.01-0.5 mg enzyme protein per g dry solid (DS).

Alpha-Amylases Present and/or Added During Saccharification and/or Fermentation (e.g. SSF)

Optionally an alpha-amylase (EC 3.2.1.1) may be added during saccharification ste (b) and/or fermentation step (c). The alpha-amylase may be of any origin, but is typically of filamentous fungus origin. According to the invention an alpha-amylases adding during saccharification and/or fermentation is typically a fungal acid alpha-amylase.

The fungal acid alpha-amylases may be an acid fungal alpha-amylase derived from a strain of the genus *Aspergillus*, such as *Aspergillus oryzae* and *Aspergillus niger*.

A suitable fungal acid alpha-amylase is one derived from a strain *Aspergillus niger*. In a preferred embodiment the fungal acid alpha-amylase is the one from *A. niger* disclosed as "AMYA_ASPNG" in the Swiss-prot/TeEMBL database under the primary accession no.

P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

The fungal acid alpha-amylase may also be a wild-type enzyme comprising a carbohydrate-binding module (CBM) and an alpha-amylase catalytic domain (i.e., a non-hybrid), or a variant thereof. In an embodiment the wild-type fungal acid alpha-amylase is derived from a strain of *Aspergillus kawachii*.

A specific example of a contemplated hybrid alpha-amylase includes the *Rhizomucor pusillus* alpha-amylase with *Aspergillus niger* glucoamylase linker and starch-binding domain (SBD) (which is disclosed in Table 5 as a combination of amino acid sequences SEQ ID NO: 20, SEQ ID NO: 72 and SEQ ID NO: 96 in U.S. application Ser. No. 11/316,535) (hereby incorporated by reference), and shown as SEQ ID NO: 3 herein. In another embodiment the hybrid fungal acid alpha-amylase is a *Meripilus giganteus* alpha-amylase with *Athelia rolfsii* glucoamylase linker and SBD (SEQ ID NO: 102 in U.S. 60/638,614) (hereby incorporated by reference). Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain.

In a preferred embodiment the fungal acid alpha-amylase is one disclosed in WO 2013/006756 including the following variants: *Rhizomucor pusillus* alpha-amylase variant having an *Aspergillus niger* glucoamylase linker and starch-binding domain (SBD) which further comprises at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 3 herein for numbering) (all incorporated by reference).

An acid alpha-amylases may according to the invention be added in an amount of 0.1 to 10 AFAU/g DS, preferably 0.10 to 5 AFAU/g DS, especially 0.3 to 2 AFAU/g DS.

Fermenting Organisms

Examples of fermenting organisms used in fermentation step (c) or simultaneous saccharification and fermentation (i.e., SSF) for converting fermentable sugars in the fermentation medium into ethanol include fungal organisms, such as especially yeast. Preferred yeast includes strains of *Saccharomyces* spp., in particular, *Saccharomyces cerevisiae*.

In one embodiment the fermenting organism may be added to the fermentation medium, so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used as starting material according to the present invention. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley.

Fermentation Products

According to the invention ethanol is produced. Ethanol produced according to the invention may be used as fuel which may be blended with gasoline. However, ethanol may also be used as potable ethanol.

Recovery

Subsequent to fermentation the ethanol may be separated from the fermentation medium, e.g., by distillation. Alternatively the ethanol may be extracted from the fermentation medium by micro or membrane filtration techniques. The ethanol may also be recovered by stripping or other method well known in the art.

Use of Phospholipase a and/or Phospholipase C for Reducing Foam During Fermentation In a final aspect, the invention relates to the use of phospholipase A and/or phospholipase C for reducing foam during ethanol fermentation.

PREFERRED EMBODIMENTS OF THE INVENTION

In a preferred embodiment the invention relates to processes of producing ethanol, comprising
(a) converting a starch-containing material into dextrins with an alpha-amylase and a protease;
(b) saccharifying the dextrins using a carbohydrate-source generating enzyme, in particular a glucoamylase, to form fermentable sugars;
(c) fermenting the fermentable sugars into ethanol using a fermenting organism, in particular yeast; wherein a phospholipase A is present and/or added during steps (b) and/or (c).

In another preferred embodiment the invention relates to processes of producing ethanol, comprising
(a) converting a starch-containing material into dextrins with a *Bacillus* alpha-amylase and a *Pyrococcus* protease;
(b) saccharifying the dextrins using a carbohydrate-source generating enzyme, in particular a glucoamylase, to form fermentable sugars;
(c) fermenting the fermentable sugars into ethanol using a fermenting organism, in particular yeast; wherein a phospholipase A and/or phospholipase C is(are) present and/or added during steps (b) and/or (c).

In another preferred embodiment the invention relates to processes of producing ethanol, comprising
(a) converting a starch-containing material into dextrins with:
the alpha-amylase shown as SEQ ID NO: 1 or an alpha-amylase having at least 60%, at least 70%, at least 80%, at least 90%, at least 95%, at least 97%, at least 99% sequence identity to SEQ ID NO: 1, and
the protease shown as SEQ ID NO: 4 or a protease having at least 60%, at least 70%, at least 80%, at least 90%, at least 95%, at least 97%, at least 99% sequence identity to SEQ ID NO: 4;
(b) saccharifying the dextrins using a carbohydrate-source generating enzyme, in particular a glucoamylase, to form fermentable sugars;
(c) fermenting the fermentable sugars into ethanol using a fermenting organism; wherein
the phospholipase A shown as SEQ ID NO: 2 or a phospholipase A having at least 60%, at least 70%, at least 80%, at least 90%, at least 95%, at least 97%, at least 99% sequence identity to SEQ ID NO: 2
is present and/or added during steps (b) and/or (c).

In another preferred embodiment the invention relates to processes of producing ethanol, comprising
(b) converting a starch-containing material into dextrins with:
the alpha-amylase shown as SEQ ID NO: 1 or an alpha-amylase having at least 60%, at least 70%, at least 80%, at least 90%, at least 95%, at least 97%, at least 99% sequence identity to SEQ ID NO: 1, and
the protease shown as SEQ ID NO: 4 or a protease having at least 60%, at least 70%, at least 80%, at least 90%, at least 95%, at least 97%, at least 99% sequence identity to SEQ ID NO: 4;
(b) saccharifying the dextrins using a carbohydrate-source generating enzyme, in particular a glucoamylase, to form fermentable sugars;
(c) fermenting the fermentable sugars into ethanol using a fermenting organism; wherein
the phospholipase C shown as SEQ ID NO: 7 or a phospholipase A having at least 60%, at least 70%, at least 80%, at least 90%, at least 95%, at least 97%, at least 99% sequence identity to SEQ ID NO: 7
is present and/or added during steps (b) and/or (c).

In another preferred embodiment the invention relates to processes of producing ethanol, comprising
(c) converting a starch-containing material into dextrins with:
the alpha-amylase shown as SEQ ID NO: 1 or an alpha-amylase having at least 60%, at least 70%, at least 80%, at least 90%, at least 95%, at least 97%, at least 99% sequence identity to SEQ ID NO: 1, and
the protease shown as SEQ ID NO: 4 or a protease having at least 60%, at least 70%, at least 80%, at least 90%, at least 95%, at least 97%, at least 99% sequence identity to SEQ ID NO: 4;
(b) saccharifying the dextrins using a carbohydrate-source generating enzyme, in particular a glucoamylase, to form fermentable sugars;
(c) fermenting the fermentable sugars into ethanol using a fermenting organism;
wherein
the phospholipase A shown as SEQ ID NO: 2 or a phospholipase A having at least 60%, at least 70%, at least 80%, at least 90%, at least 95%, at least 97%, at least 99% sequence identity to SEQ ID NO: 2, and
the phospholipase C shown as SEQ ID NO: 7 or a phospholipase A having at least 60%, at least 70%, at least 80%, at least 90%, at least 95%, at least 97%, at least 99% sequence identity to SEQ ID NO: 7
are present and/or added during steps (b) and/or (c).

The invention is further summarized in the following paragraphs:

1. Method of reducing foam during ethanol fermentation, wherein a phospholipase A and/or a phospholipase C is(are) present and/or added during fermentation.

2. The method of paragraph 1, wherein the phospholipase A, e.g., one derived from a strain of *Talaromyces*, in particular *Talaromyces leycettanus*, is the mature part of the sequence shown as SEQ ID NO: 2, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

3. The method of paragraphs 1 or 2, wherein the phospholipase C, e.g., one derived from a strain of *Bacillus*, in particular *Bacillus thuringiensis*, is the mature part of the sequence shown as SEQ ID NO: 7, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

4. The method of any of paragraphs 1-3, wherein the phospholipase A shown in SEQ ID NO: 2 and phospholipase C shown in SEQ ID NO: 7 are present and/or added during fermentation.

5. The method of any of paragraphs 1-4, wherein the fermentation is carried in a fermentation medium comprising a fermenting organism, in particular yeast, and fermentable sugars.

6. The method of any of paragraphs 1-5, wherein the fermentation is carried out in a fermentation medium comprising fermentable sugars derived from saccharifying starch-containing material with a carbohydrate-source generating enzyme, in particular a glucoamylase, and optionally an alpha-amylase.

7. The method of any of paragraphs 1-6, wherein the fermentation is carried out in a fermentation medium comprising fermentable sugars derived from starch-containing material liquefied with an alpha-amylase and optionally a protease.

8. The method of any of paragraphs 1-7, wherein the fermentation is carried out in a fermentation medium comprising fermentable sugars derived from starch-containing material first liquefied with an alpha-amylase and a protease and then saccharified with a carbohydrate-source generating enzyme, in particular a glucoamylase.

9. The method of paragraphs 7 or 8, wherein liquefaction is carried out at a temperature above the initial gelatinization temperature, such as at a temperature between 70 and 100° C., such as between 80-90° C., such as around 85° C., before being saccharified.

10. The method of any of paragraphs 6-9, wherein the alpha-amylase is a bacterial alpha-amylase, wherein the bacterial alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular a truncated *Bacillus stearothermophilus* alpha-amylase, preferably having from 485-495 amino acids, such as around 491 amino acids.

11. The method of paragraph 10, wherein the *Bacillus stearothermophilus* alpha-amylase is the one shown as SEQ ID NO: 1 herein or one having sequence identity to SEQ ID NO: 1 of at least 60%, at least 70%, at least 80%, at least 90%, at least 95%, at least 96%, at least 97%, at least 98%, at least 99%.

12. The method of paragraph 10 or 11, wherein the Bacillus stearothermophilus alpha-amylase variants has one of the following sets of mutations:
I181*+G182*;
I181*+G182*+N193F; preferably
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 1 for numbering).

13. The method of any of paragraphs 9-12, wherein the Bacillus stearothermophilus alpha-amylase variant has a sequence identity to SEQ ID NO: 1 of at least 60%, at least 70%, at least 80%, at least 90%, at least 95%, at least 96%, at least 97%, at least 98%, at least 99%, but less than 100%.

14. The method of any of paragraphs 7-13, wherein the protease is a bacterial protease, in particular a Pyrococcus protease, especially Pyrococcus furiosus protease, such as the one shown as SEQ ID NO: 4.

15. The method of paragraph 14, wherein the protease is the one shown SEQ ID NO: 4 herein, or wherein the protease has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 4 herein.

16. A process of producing ethanol, comprising
(a) converting a starch-containing material into dextrins with an alpha-amylase;
(b) saccharifying the dextrins using a carbohydrate-source generating enzyme, to form fermentable sugars;
(c) fermenting the fermentable sugars into ethanol using a fermenting organism; wherein a phospholipase A and/or a phospholipase C is(are) present and/or added during steps (b) and/or (c).

17. The process of paragraph 16, wherein the phospholipase A, e.g., one derived from a strain of Talaromyces, in particular Talaromyces leycettanus, is the mature part of the sequence shown as SEQ ID NO: 2 or one having a sequence identity thereto of at least 60%, at least 65%, at least 70%, at least 75%, at least 80%, at least 85%, at least 90%, at least 95%, at least 96%, at least 97%, at least 98%, at least 99%.

18. The process of paragraphs 16 or 17, wherein the phospholipase C, e.g., one derived from a strain of Bacillus, in particular Bacillus thuringiensis, is the mature part of the sequence shown as SEQ ID NO: 7, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

19. The process of any of paragraphs 16-18, wherein the phospholipase A shown in SEQ ID NO: 2 and phospholipase C shown in SEQ ID NO: 7 are present and/or added during fermentation.

20. The process of paragraphs 16-19, wherein the phospholipase A and/or phospholipase C is(are) present and/or added during simultaneous saccharification and fermentation (SSF) (i.e., simultaneous steps (b) and/or (c)).

21. The process of any of paragraphs 16-20, wherein step (a) is a liquefaction step carried out at a temperature above the initial gelatinization temperature, such as at a temperature between 70 and 100° C., in particular between 80-90° C., such as around 85° C.

22. The process of any of paragraphs 16-21, wherein a protease is present and/or added during step (a).

23. The process of any of paragraphs 16-22, wherein the alpha-amylase used in step (a) is a bacterial alpha-amylase, wherein the bacterial alpha-amylase is derived from the genus Bacillus, such as a strain of Bacillus stearothermophilus, in particular a variant of a Bacillus stearothermophilus alpha-amylase, such as the one shown in SEQ ID NO: 3 in WO 99/019467 or SEQ ID NO: 1 herein, in particular a truncated Bacillus stearothermophilus alpha-amylase, preferably having from 485-495 amino acids, such as around 491 amino acids.

24. The process of paragraph 23, wherein Bacillus stearothermophilus alpha-amylase is the one shown as SEQ ID NO: 1 or one having a sequence identity thereto of at least 60%, at least 70%, at least 80%, at least 90%, at least 95%, at least 96%, at least 97%, at least 98%, at least 99%.

25. The process of paragraphs 23 or 24, wherein the Bacillus stearothermophilus alpha-amylase variant has one of the following sets of mutations:
I181*+G182*;
I181*+G182*+N193F; preferably
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 1 for numbering).

26. The process of any of paragraphs 23-25, wherein the Bacillus stearothermophilus alpha-amylase variant has a sequence identity to SEQ ID NO: 1 of at least 60%, at least 70%, at least 80%, at least 90%, at least 95%, at least 96%, at least 97%, at least 98%, at least 99%, but less than 100%.

27. The process of any of paragraphs 22-26, wherein the protease is a bacterial protease, in particular a Pyrococcus protease, especially Pyrococcus furiosus protease, such as the one shown as SEQ ID NO: 4 herein.

28. The process of paragraph 27, wherein the protease is the one shown SEQ ID NO: 4 herein, or wherein the protease has at least 60%, such as at least 70%, such as at least 80%, such as at least 85%, such as at least 90%, such as at least 95%, such as at least 96%, such as at least 97%, such as at least 98%, such as at least 99% identity to SEQ ID NO: 4.

29. Use of a phospholipase A and/or a phospholipase C for reducing foaming during ethanol fermentation.

30. The use according to paragraph 29, wherein the phospholipase A, e.g., one derived from a strain of Talaromyces, in particular Talaromyces leycettanus, is the mature part of the sequence shown as SEQ ID NO: 2, or one having a sequence identity thereto of at least 60%, at least 65%, at least 70%, at least 75%, at least 80%, at least 85%, at least 90%, at least 95%, at least 96%, at least 97%, at least 98%, at least 99%.

31. The use of paragraph 29, wherein the phospholipase C, e.g., one derived from a strain of Bacillus, in particular Bacillus thuringiensis, is the mature part of the sequence shown as SEQ ID NO: 7, or a sequence having a sequence identity thereto of at least 60%, at least 65%, at least 70%, at least 75%, at least 80%, at least 85%, at least 90%, at least 95%, at least 96%, at least 97%, at least 98%, at least 99%.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Material & Methods

Phospholipase A derived from *Talaromyces leycettanus* as shown as SEQ ID NO: 2. (P23XQ7)

Phospholipase C derived from *Bacillus thuringiensis* as shown in SEQ ID NO: 7 (P3352W).

Phospholipase A derived from *Thermomyces lanuginosus* as shown in SEQ ID NO: 8 (P4NM).

Alpha-Amylase 369: (AA369): *Bacillus stearothermophilus* alpha-amylase with the mutations: I181*+G182*+N193F+V59A+Q89R+E129V+K177L+R179E+Q254S+M284V truncated to be around 491 amino acids long (SEQ ID NO: 1 herein).

Protease PF ("PF"): Protease derived from the bacterium *Pyrococcus furiosus* shown in SEQ ID NO: 4 herein.

Glucoamylase SA ("GSA"): Blend comprising *Talaromyces emersonii* glucoamylase disclosed as SEQ ID NO: 34 in WO99/28448, *Trametes cingulata* glucoamylase disclosed as SEQ ID NO: 2 in WO 06/69289, and *Rhizomucor pusillus* alpha-amylase with *Aspergillus niger* glucoamylase linker and SBD disclosed as SEQ ID NO: 3 herein with the following substitutions: G128D+D143N (activity ratio AGU:AGU:FAU(F): approx. 30:7:1).

RED STAR™: *Saccharomyces cerevisiae* from Fermentis/Lesaffre, USA,

Methods:

Identity: The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98). FASTA protein alignments use the Smith-Waterman algorithm with no limitation on gap size (see "Smith-Waterman algorithm", T. F. Smith and M. S. Waterman (1981) J. Mol. Biol. 147:195-197).

Determination of Acid Amylolytic Activity (FAU)

One Fungal Alpha-Amylase Unit (1 FAU) is defined as the amount of enzyme, which breaks down 5.26 g starch (Merck Amylum solubile Erg. B.6, Batch 9947275) per hour at Novozymes' standard method for determination of alpha-amylase based upon the following standard conditions:

| Substrate | Soluble starch |
| --- | --- |
| Temperature | 37° C. |
| pH | 4.7 |
| Reaction time | 7-20 minutes |

A detailed description of Novozymes' method for determining KNU and FAU is available on request as standard method EB-SM-0009.02/01. Determination of acid alpha-amylase activity (AFAU) Acid alpha-amylase activity is measured in AFAU (Acid Fungal Alpha-amylase Units), which are determined relative to an enzyme standard.

The standard used is AMG 300 L (wild type *A. niger* G1 AMG sold by Novozymes A/S).

The neutral alpha-amylase in this AMG falls after storage at room temperature for 3 weeks from approx. 1 FAU/mL to below 0.05 FAU/mL.

The acid alpha-amylase activity in this AMG standard is determined in accordance with AF 9⅓ (Novo method for the determination of fungal alpha-amylase). In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

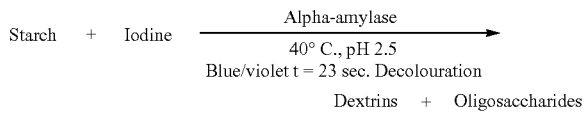

Starch + Iodine $\xrightarrow[\text{40° C., pH 2.5}]{\text{Alpha-amylase}}$

Blue/violet t = 23 sec. Decolouration

Dextrins + Oligosaccharides

Standard conditions/reaction conditions: (per minute)
Substrate: starch, approx. 0.17 g/L
Buffer: Citrate, approx. 0.03 M
Iodine ($I_2$): 0.03 g/L
$CaCl_2$: 1.85 mM
pH: 2.50±0.05
Incubation temperature: 40° C.
Reaction time: 23 seconds
Wavelength: Lambda=590 nm
Enzyme concentration: 0.025 AFAU/mL
Enzyme working range: 0.01-0.04 AFAU/mL Further details can be found in standard method document EB-SM-0259.02/01 available on request from Novozymes A/S, which folder is hereby incorporated by reference.

Determination of FAU-F

FAU-F Fungal Alpha-Amylase Units (Fungamyl) is measured relative to an enzyme standard of a declared strength.

| Reaction conditions | |
| --- | --- |
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU-A)

Alpha amylase activity is measured in KNU(A) Kilo Novozymes Units (A), relative to an enzyme standard of a declared strength.

Alpha amylase in samples and α-glucosidase in the reagent kit hydrolyze the substrate (4,6-ethylidene($G_7$)-p-nitrophenyl($G_1$)-α,D-maltoheptaoside (ethylidene-$G_7$PNP) to glucose and the yellow-colored p-nitrophenol.

The rate of formation of p-nitrophenol can be observed by Konelab 30. This is an expression of the reaction rate and thereby the enzyme activity.

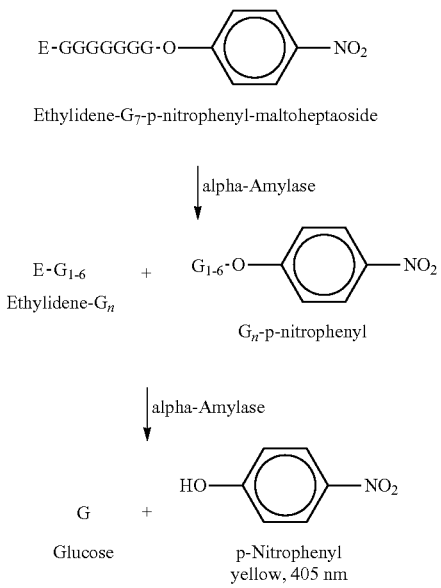

The enzyme is an alpha-amylase with the enzyme classification number EC 3.2.1.1.

| Parameter | Reaction conditions |
|---|---|
| Temperature | 37° C. |
| pH | 7.00 (at 37° C.) |
| Substrate conc. | Ethylidene-GyPNP, R2: 1.86 mM |
| Enzyme conc. (conc. of high/low standard in reaction mixture) | 1.35-4.07 KNU(A)/L |
| Reaction time | 2 min |
| Interval kinetic measuring time | 1/18 sec. |
| Wave length | 405 nm |
| Conc. of reagents/chemicals critical for the analysis | α-glucosidase, R1: ≥3.39 kU/L |

A folder EB-SM-5091.02-D on determining KNU-A activity is available upon request to Novozymes A/S, Denmark, which folder is hereby included by reference.

Determination of FAU(F)

FAU(F) Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Glucoamylase and Alpha-Glucosidase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

AMG Incubation:

| | |
|---|---|
| Substrate: | maltose 23.2 mM |
| Buffer: acetate | 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

Color Reaction:

| | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

EXAMPLES

Example 1

Defoaming Using Fermentation Using *Talaromyces leycettanus* PLA (SEQ ID NO: 2) and/or *Bacillus thuringiensis* PLC (SEQ ID NO: 7) on Corn Mash Liquefied Using Alpha-Amylase and Protease Ground corn was liquefied using 2.1 μg EP AA369/gDS and 3 μg EP PFU/g DS. Liquefied corn mash was transferred in frozen state to the lab and thawed. Around 125 g of liquefied corn mash was aliquot to the 250 mL of flasks. The mash was prepared to 200 ppm urea and 3 ppm penicillin using 200 g/L urea and 1 g/L penicillin, respectively. The mash was adjusted to pH 5 using 40% v/v $H_2SO_4$ and the dry solids content of the mash was measured on a Mettler- Toledo moisture balance, with a value of 32.80% DS. RED STAR™ yeast was rehydrated with 2.75 g of yeast placed in 50 mL of 32° C. tap water for 30 minutes. While the yeast soaked, each mash sample was dosed with Glucoamylase SA (0.6 AGU/gDS), as calculated by the following equation.

$$\text{Enz. dose (ml)} = \frac{\text{Final enz. dose }(AGU/\text{gDS}) \times \text{Mash weight} \times \text{Solid content }(\% \text{ DS}/100)}{\text{Conc. enzyme }(AGU/\text{ml})}$$

Phospholipase A (PLA) and/or phospholipase C (PLC) were dosed as shown in Table 1. The unit for the dose is µg enzyme protein/g dry solids (DS) of corn mash.

TABLE 1

Dosage of various PLA/PLC as defoamer

| Defoamer | Dose |
|---|---|
| Control | 0 |
| Thela PLA | 0.105 |
| Talle PLA | 0.105 |
| Bt PLC | 0.105 |
| Thela PLA + Bt PLC | 0.053 + 0.053 |
| Talle PLA + Bt PLC | 0.053 + 0.053 |

All samples were dosed with 100 µL of yeast solution at time zero, vortexed, and placed in a water bath. The simultaneous saccharification and fermentation (SSF) was carried out at 32° C. for 53 hours with continuously stirring. The foam formation was observed and recorded after 7 hours of SSF.

At 53 hours of fermentation, samples were sacrificed for HPLC analysis. Each sample was dosed with 50 µL of 40% sulfuric acid, vortexed, and centrifuged for 10 minutes at 3000 g before being filtered into HPLC vials through 0.45 µm filters.

The following HPLC system was used:

TABLE 2

Analysis of HPLC system

| | |
|---|---|
| HPLC system | Agilent's 1100/1200 series with Chem station software<br>Degasser<br>Quaternary Pump<br>Auto-Sampler<br>Column Compartment/w Heater<br>Refractive Index Detector (RI) |
| Column | Bio-Rad HPX- 87H Ion Exclusion Column 300 mm × 7.8 mm parts# 125-0140<br>Bio-Rad guard cartridge cation H parts# 125-0129, Holder parts# 125-0131 |
| Method | 0.005M $H_2SO_4$ mobile phase<br>Flow rate of 0.6 ml/min<br>Column temperature - 65° C.<br>RI detector temperature - 55° C. |

The method quantifies analytes using calibration standards for dextrins (DP4+), maltotriose, maltose, glucose, fructose, acetic acid, lactic acid, glycerol and ethanol. A 4 point calibration including the origin is used.

The rest of the samples were then evaporated on a Buchi Multivapor for distillation of ethanol. FIG. 1 shows the foaming after 7 hours of simultaneous saccharification and fermentation (SSF). The control sample without any PLA/PLC dosage generated the highest level of foams, approximately over 2 cm of foams in height. All the other samples with phospholipase treatments showed defoaming effect from the enzymes. The Talle PLA, Bt PLC and their combinations showed better defoaming effect than Thela PLA alone, given no visible foams inside of the flask.

The invention claimed is:

1. A process of producing ethanol, comprising:
(a) liquefying a starch-containing material into dextrins with an alpha-amylase at a temperature between 70° C. and 100° C.;
(b) saccharifying the dextrins with a glucoamylase to form fermentable sugars; and
(c) fermenting the fermentable sugars into ethanol with a fermenting organism;
wherein saccharifying step (b) and fermenting step (c) are carried out as a simultaneous saccharification and fermentation (SSF); and
wherein a phospholipase C having an amino acid sequence that is at least 90% identical to the amino acid sequence set forth in SEQ ID NO: 7 is present or added during SSF.

2. The process of claim 1, wherein the phospholipase C has an amino acid sequence that is at least 95% identical to the amino acid sequence set forth in SEQ ID NO: 7.

3. The process of claim 1, wherein the phospholipase C has an amino acid sequence that is at least 97% identical to the amino acid sequence set forth in SEQ ID NO: 7.

4. The process of claim 1, wherein the phospholipase C has an amino acid sequence that is at least 99% identical to the amino acid sequence set forth in SEQ ID NO: 7.

5. The process of claim 1, wherein a protease is present or added during step (a).

6. The process of claim 1, wherein the alpha-amylase used in step (a) is a bacterial alpha-amylase.

7. The process of claim 1, wherein the starch-containing material is corn.

8. A process of producing ethanol, comprising:
(a) liquefying a starch-containing material into dextrins with an alpha-amylase at a temperature between 70° C. and 100° C.;
(b) saccharifying the dextrins with a glucoamylase to form fermentable sugars; and
(c) fermenting the fermentable sugars into ethanol with a fermenting organism;
wherein saccharifying step (b) and fermenting step (c) are carried out as a simultaneous saccharification and fermentation (SSF); and
wherein a phospholipase A having an amino acid sequence that is at least 90% identical to the amino acid sequence set forth in SEQ ID NO: 2 is present or added during SSF.

9. The process of claim 8, wherein the phospholipase A has an amino acid sequence that is at least 95% identical to the amino acid sequence set forth in SEQ ID NO: 2.

10. The process of claim 8, wherein the phospholipase A has an amino acid sequence that is at least 97% identical to the amino acid sequence set forth in SEQ ID NO: 2.

11. The process of claim 8, wherein the phospholipase A has an amino acid sequence that is at least 99% identical to the amino acid sequence set forth in SEQ ID NO: 2.

12. The process of claim 8, wherein a protease is present or added during step (a).

13. The process of claim 8, wherein the alpha-amylase used in step (a) is a bacterial alpha-amylase.

14. The process of claim 8, wherein the starch-containing material is corn.

15. A process of producing ethanol, comprising:
(a) liquefying a starch-containing material into dextrins with an alpha-amylase at a temperature between 70° C. and 100° C.;
(b) saccharifying the dextrins with a glucoamylase to form fermentable sugars; and
(c) fermenting the fermentable sugars into ethanol with a fermenting organism;
wherein saccharifying step (b) and fermenting step (c) are carried out as a simultaneous saccharification and fermentation (SSF); and
wherein a phospholipase A and a phospholipase C are present or added during SSF.

16. The process of claim 15, wherein the phospholipase A has an amino acid sequence that is at least 90% identical to the amino acid sequence set forth in SEQ ID NO: 2 and wherein the phospholipase C has an amino acid sequence that is at least 90% identical to the amino acid sequence set forth in SEQ ID NO: 7.

17. The process of claim 15, wherein the phospholipase A has an amino acid sequence that is at least 95% identical to the amino acid sequence set forth in SEQ ID NO: 2 and wherein the phospholipase C has an amino acid sequence that is at least 95% identical to the amino acid sequence set forth in SEQ ID NO: 7.

18. The process of claim 15, wherein the phospholipase A has an amino acid sequence that is at least 97% identical to the amino acid sequence set forth in SEQ ID NO: 2 and wherein the phospholipase C has an amino acid sequence that is at least 97% identical to the amino acid sequence set forth in SEQ ID NO: 7.

19. The process of claim 15, wherein the phospholipase A has an amino acid sequence that is at least 99% identical to the amino acid sequence set forth in SEQ ID NO: 2 and wherein the phospholipase C has an amino acid sequence that is at least 99% identical to the amino acid sequence set forth in SEQ ID NO: 7.

20. The process of claim 15, wherein the phospholipase A has the amino acid sequence set forth in SEQ ID NO: 8 and wherein the phospholipase C has the amino acid sequence set forth in SEQ ID NO: 7.

21. The process of claim 15, wherein a protease is present or added during step (a).

22. The process of claim 15, wherein the alpha-amylase used in step (a) is a bacterial alpha-amylase.

* * * * *

SEQUENCE LISTING

```
<160> NUMBER OF SEQ ID NOS: 8

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110
```

```
Thr Glu Trp Val Asp Ala Val Glu Val Asn Pro Ser Asp Arg Asn Gln
            115                 120                 125
Glu Ile Ser Gly Thr Tyr Gln Ile Gln Ala Trp Thr Lys Phe Asp Phe
130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
            180                 185                 190
Asn Gly Asn Tyr Asp Tyr Leu Met Tyr Ala Asp Leu Asp Met Asp His
        195                 200                 205
Pro Glu Val Val Thr Glu Leu Lys Asn Trp Gly Lys Trp Tyr Val Asn
210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                245                 250                 255
Lys Pro Leu Phe Thr Val Gly Glu Tyr Trp Ser Tyr Asp Ile Asn Lys
            260                 265                 270
Leu His Asn Tyr Ile Thr Lys Thr Asn Gly Thr Met Ser Leu Phe Asp
        275                 280                 285
Ala Pro Leu His Asn Lys Phe Tyr Thr Ala Ser Lys Ser Gly Gly Ala
        290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
        355                 360                 365
Tyr Tyr Gly Ile Pro Gln Tyr Asn Ile Pro Ser Leu Lys Ser Lys Ile
        370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
        435                 440                 445
Phe Tyr Asp Leu Thr Gly Asn Arg Ser Asp Thr Val Thr Ile Asn Ser
        450                 455                 460
Asp Gly Trp Gly Glu Phe Lys Val Asn Gly Gly Ser Val Ser Val Trp
465                 470                 475                 480
Val Pro Arg Lys Thr Val Ser Thr Ile Ala Arg Pro Ile Thr Thr
                485                 490                 495
Arg Pro Trp Thr Gly Glu Phe Val Arg Trp Thr Glu Pro Arg Leu Val
                500                 505                 510
Ala Trp Pro
            515
```

```
<210> SEQ ID NO 2
<211> LENGTH: 296
<212> TYPE: PRT
<213> ORGANISM: Talaromyces leycettanus
<220> FEATURE:
<221> NAME/KEY: SIGNAL
<222> LOCATION: (1)..(19)
<220> FEATURE:
<221> NAME/KEY: mat_peptide
<222> LOCATION: (20)..(296)

<400> SEQUENCE: 2

Met His Arg Pro Leu Gln Leu Trp Ala Leu Ala Ala Leu Thr Ser Leu
                -15                 -10                  -5

Val Thr Ala Ala Pro Ala Pro Val Leu Arg Arg Asp Val Ser Ser Ser
            -1   1               5                  10

Val Leu Ser Glu Leu Asp Leu Phe Ala Gln Tyr Ser Ala Ala Ala Tyr
         15                  20                  25

Cys Ser Ser Asn Ile Gly Ser Pro Gly Thr Lys Leu Thr Cys Ser Val
 30                  35                  40                  45

Gly Asn Cys Pro Arg Val Glu Ala Ala Asp Thr Glu Thr Leu Ile Glu
                 50                  55                  60

Phe Asn Glu Ser Ser Ser Phe Gly Asp Val Thr Gly Tyr Ile Ala Val
             65                  70                  75

Asp Arg Thr Asn Ser Leu Leu Val Leu Ala Phe Arg Gly Ser Ser Thr
             80                  85                  90

Val Ser Asn Trp Glu Ala Asp Leu Asp Phe Pro Leu Thr Asp Ala Ser
 95                 100                 105

Ser Leu Cys Ser Gly Cys Glu Ile His Ser Gly Phe Trp Ala Ala Trp
110                 115                 120                 125

Gln Thr Val Gln Ala Ser Ile Thr Ser Thr Leu Glu Ser Ala Ile Ala
                130                 135                 140

Ser Tyr Pro Gly Tyr Thr Leu Val Phe Thr Gly His Ser Tyr Gly Ala
                145                 150                 155

Ala Leu Ala Ala Ile Ala Ala Thr Thr Leu Arg Asn Ala Gly Tyr Thr
                160                 165                 170

Ile Gln Leu Tyr Asp Tyr Gly Gln Pro Arg Leu Gly Asn Leu Ala Leu
175                 180                 185

Ala Gln Tyr Ile Thr Ala Gln Thr Gln Gly Ala Asn Tyr Arg Val Thr
190                 195                 200                 205

His Thr Asp Asp Ile Val Pro Lys Leu Pro Pro Glu Leu Phe Gly Tyr
                210                 215                 220

His His Phe Ser Pro Glu Tyr Trp Ile Thr Ser Gly Asp Asn Val Thr
                225                 230                 235

Val Thr Thr Ser Asp Val Gln Val Val Thr Gly Ile Asp Ser Thr Ala
                240                 245                 250

Gly Asn Asp Gly Thr Leu Leu Asp Ser Thr Ser Ala His Asp Trp Tyr
                255                 260                 265

Ile Val Tyr Ile Asp Gly Cys Asp
270                 275

<210> SEQ ID NO 3
<211> LENGTH: 583
<212> TYPE: PRT
<213> ORGANISM: Artificial Sequence
<220> FEATURE:
<223> OTHER INFORMATION: Hybrid protein sequence

<400> SEQUENCE: 3
```

-continued

```
Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
                100                 105                 110

Asn His Ala Gly Pro Thr Ser Asn Gly Tyr Ser Gly Tyr Thr Phe Gly
            115                 120                 125

Asp Ala Ser Leu Tyr His Pro Lys Cys Thr Ile Asp Tyr Asn Asp Gln
130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
                180                 185                 190

His Ile Arg Lys Asp Phe Trp Thr Gly Tyr Ala Glu Ala Ala Gly Val
            195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
    275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
        355                 360                 365

Ala Tyr Ala Phe Lys His Gly Asp Ala Leu Val Val Leu Asn Asn Tyr
    370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415
```

```
Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
        435                 440                 445

Thr Gly Ser Gly Ser Val Thr Ser Thr Ser Lys Thr Thr Ala Thr Ala
450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
            485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
            530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 4
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 4

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
```

```
                180                 185                 190
Tyr Asp Val Ile Thr Ser Phe Ser Ser Arg Gly Pro Thr Ala Asp Gly
                195                 200                 205

Arg Leu Lys Pro Glu Val Val Ala Pro Gly Asn Trp Ile Ile Ala Ala
            210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
        290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
            355                 360                 365

Gly Phe Glu Lys Val Gly Tyr Tyr Asn Pro Thr Asp Gly Thr Trp Thr
        370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 5
<211> LENGTH: 573
<212> TYPE: PRT
<213> ORGANISM: Gloeophyllum sepiarium
<220> FEATURE:
<221> NAME/KEY: SIGNAL
<222> LOCATION: (1)..(17)
<220> FEATURE:
<221> NAME/KEY: mat_peptide
<222> LOCATION: (18)..(573)

<400> SEQUENCE: 5

Met Tyr Arg Phe Leu Val Cys Ala Leu Gly Leu Ala Ala Ser Val Leu
        -15                 -10                  -5

Ala Gln Ser Val Asp Ser Tyr Val Ser Ser Glu Gly Pro Ile Ala Lys
 -1  1               5                  10                  15

Ala Gly Val Leu Ala Asn Ile Gly Pro Asn Gly Ser Lys Ala Ser Gly
                20                  25                  30

Ala Ser Ala Gly Val Val Ala Ser Pro Ser Thr Ser Asp Pro Asp
            35                  40                  45

Tyr Trp Tyr Thr Trp Thr Arg Asp Ser Ser Leu Val Phe Lys Ser Leu
        50                  55                  60

Ile Asp Gln Tyr Thr Thr Gly Ile Asp Ser Thr Ser Ser Leu Arg Thr
    65                  70                  75

Leu Ile Asp Asp Phe Val Thr Ala Glu Ala Asn Leu Gln Gln Val Ser
80                  85                  90                  95
```

-continued

```
Asn Pro Ser Gly Thr Leu Thr Thr Gly Gly Leu Gly Glu Pro Lys Phe
                100                 105                 110
Asn Val Asp Glu Thr Ala Phe Thr Gly Ala Trp Gly Arg Pro Gln Arg
            115                 120                 125
Asp Gly Pro Ala Leu Arg Ser Thr Ala Leu Ile Thr Tyr Gly Asn Trp
        130                 135                 140
Leu Leu Ser Asn Gly Asn Thr Ser Tyr Val Thr Ser Asn Leu Trp Pro
    145                 150                 155
Ile Ile Gln Asn Asp Leu Gly Tyr Val Val Ser Tyr Trp Asn Gln Ser
160                 165                 170                 175
Thr Tyr Asp Leu Trp Glu Glu Val Asp Ser Ser Ser Phe Phe Thr Thr
                180                 185                 190
Ala Val Gln His Arg Ala Leu Arg Glu Gly Ala Ala Phe Ala Thr Ala
            195                 200                 205
Ile Gly Gln Thr Ser Gln Val Ser Ser Tyr Thr Thr Gln Ala Asp Asn
        210                 215                 220
Leu Leu Cys Phe Leu Gln Ser Tyr Trp Asn Pro Ser Gly Gly Tyr Ile
    225                 230                 235
Thr Ala Asn Thr Gly Gly Gly Arg Ser Gly Lys Asp Ala Asn Thr Leu
240                 245                 250                 255
Leu Ala Ser Ile His Thr Tyr Asp Pro Ser Ala Gly Cys Asp Ala Ala
                260                 265                 270
Thr Phe Gln Pro Cys Ser Asp Lys Ala Leu Ser Asn Leu Lys Val Tyr
            275                 280                 285
Val Asp Ser Phe Arg Ser Val Tyr Ser Ile Asn Ser Gly Val Ala Ser
        290                 295                 300
Asn Ala Ala Val Ala Thr Gly Arg Tyr Pro Glu Asp Ser Tyr Gln Gly
305                 310                 315
Gly Asn Pro Trp Tyr Leu Thr Thr Phe Ala Val Ala Glu Gln Leu Tyr
320                 325                 330                 335
Asp Ala Leu Asn Val Trp Glu Ser Gln Gly Ser Leu Glu Val Thr Ser
                340                 345                 350
Thr Ser Leu Ala Phe Phe Gln Gln Phe Ser Ser Gly Val Thr Ala Gly
            355                 360                 365
Thr Tyr Ser Ser Ser Ser Ser Thr Tyr Ser Thr Leu Thr Ser Ala Ile
        370                 375                 380
Lys Asn Phe Ala Asp Gly Phe Val Ala Ile Asn Ala Lys Tyr Thr Pro
    385                 390                 395
Ser Asn Gly Gly Leu Ala Glu Gln Tyr Ser Lys Ser Asp Gly Ser Pro
400                 405                 410                 415
Leu Ser Ala Val Asp Leu Thr Trp Ser Tyr Ala Ser Ala Leu Thr Ala
                420                 425                 430
Phe Glu Ala Arg Asn Asn Thr Gln Phe Ala Gly Trp Gly Ala Ala Gly
            435                 440                 445
Leu Thr Val Pro Ser Ser Cys Ser Gly Asn Ser Gly Pro Thr Val
    450                 455                 460
Ala Val Thr Phe Asn Val Asn Ala Glu Thr Val Trp Gly Glu Asn Ile
465                 470                 475
Tyr Leu Thr Gly Ser Val Asp Ala Leu Glu Asn Trp Ser Ala Asp Asn
480                 485                 490                 495
Ala Leu Leu Leu Ser Ser Ala Asn Tyr Pro Thr Trp Ser Ile Thr Val
                500                 505                 510
Asn Leu Pro Ala Ser Thr Ala Ile Glu Tyr Lys Tyr Ile Arg Lys Asn
```

```
                  515                 520                 525
Asn Gly Ala Val Thr Trp Glu Ser Asp Pro Asn Asn Ser Ile Thr Thr
            530                 535                 540

Pro Ala Ser Gly Ser Thr Thr Glu Asn Asp Thr Trp Arg
        545                 550                 555

<210> SEQ ID NO 6
<211> LENGTH: 573
<212> TYPE: PRT
<213> ORGANISM: Pycnoporus sanguineus
<220> FEATURE:
<221> NAME/KEY: SIGNAL
<222> LOCATION: (1)..(18)
<220> FEATURE:
<221> NAME/KEY: mat_peptide
<222> LOCATION: (19)..(573)

<400> SEQUENCE: 6

Met Arg Phe Thr Leu Leu Ala Ser Leu Ile Gly Leu Ala Val Gly Ala
                -15                 -10                  -5

Phe Ala Gln Ser Ser Ala Val Asp Ala Tyr Val Ala Ser Glu Ser Pro
 -1   1              5                  10

Ile Ala Lys Gln Gly Val Leu Asn Asn Ile Gly Pro Asn Gly Ser Lys
 15                  20                  25                  30

Ala His Gly Ala Lys Ala Gly Ile Val Val Ala Ser Pro Ser Thr Glu
                 35                  40                  45

Asn Pro Asp Tyr Leu Tyr Thr Trp Thr Arg Asp Ser Ser Leu Val Phe
             50                  55                  60

Lys Leu Leu Ile Asp Gln Phe Thr Ser Gly Asp Asp Thr Ser Leu Arg
         65                  70                  75

Gly Leu Ile Asp Asp Phe Thr Ser Ala Glu Ala Ile Leu Gln Gln Val
     80                  85                  90

Ser Asn Pro Ser Gly Thr Val Ser Thr Gly Gly Leu Gly Glu Pro Lys
 95                 100                 105                 110

Phe Asn Ile Asp Glu Thr Ala Phe Thr Gly Ala Trp Gly Arg Pro Gln
                115                 120                 125

Arg Asp Gly Pro Ala Leu Arg Ala Thr Ser Ile Ile Arg Tyr Ala Asn
            130                 135                 140

Trp Leu Leu Asp Asn Gly Asn Thr Thr Tyr Val Ser Asn Thr Leu Trp
        145                 150                 155

Pro Val Ile Gln Leu Asp Leu Asp Tyr Val Ala Asp Asn Trp Asn Gln
    160                 165                 170

Ser Thr Phe Asp Leu Trp Glu Glu Val Asp Ser Ser Phe Phe Thr
175                 180                 185                 190

Thr Ala Val Gln His Arg Ala Leu Arg Glu Gly Ala Thr Phe Ala Ser
                195                 200                 205

Arg Ile Gly Gln Ser Ser Val Val Ser Gly Tyr Thr Thr Gln Ala Asp
            210                 215                 220

Asn Leu Leu Cys Phe Leu Gln Ser Tyr Trp Asn Pro Ser Gly Gly Tyr
        225                 230                 235

Val Thr Ala Asn Thr Gly Gly Gly Arg Ser Gly Lys Asp Ser Asn Thr
    240                 245                 250

Val Leu Thr Ser Ile His Thr Phe Asp Pro Ala Ala Gly Cys Asp Ala
255                 260                 265                 270

Ala Thr Phe Gln Pro Cys Ser Asp Lys Ala Leu Ser Asn Leu Lys Val
                275                 280                 285
```

```
Tyr Val Asp Ala Phe Arg Ser Ile Tyr Thr Ile Asn Asn Gly Ile Ala
                290                 295                 300

Ser Asn Ala Ala Val Ala Thr Gly Arg Tyr Pro Glu Asp Ser Tyr Met
            305                 310                 315

Gly Gly Asn Pro Trp Tyr Leu Thr Thr Ser Ala Val Ala Glu Gln Leu
        320                 325                 330

Tyr Asp Ala Leu Tyr Val Trp Asp Gln Leu Gly Gly Leu Asn Val Thr
335                 340                 345                 350

Ser Thr Ser Leu Ala Phe Phe Gln Gln Phe Ala Ser Gly Leu Ser Thr
                355                 360                 365

Gly Thr Tyr Ser Ala Ser Ser Ser Thr Tyr Ala Thr Leu Thr Ser Ala
            370                 375                 380

Ile Arg Ser Phe Ala Asp Gly Phe Leu Ala Ile Asn Ala Lys Tyr Thr
        385                 390                 395

Pro Ala Asp Gly Gly Leu Ala Glu Gln Tyr Ser Arg Asn Asp Gly Thr
400                 405                 410

Pro Leu Ser Ala Val Asp Leu Thr Trp Ser Tyr Ala Ala Ala Leu Thr
415                 420                 425                 430

Ala Phe Ala Ala Arg Glu Gly Lys Thr Tyr Gly Ser Trp Gly Ala Ala
                435                 440                 445

Gly Leu Thr Val Pro Ala Ser Cys Ser Gly Gly Gly Ala Thr Val
            450                 455                 460

Ala Val Thr Phe Asn Val Gln Ala Thr Thr Val Phe Gly Glu Asn Ile
        465                 470                 475

Tyr Ile Thr Gly Ser Val Ala Ala Leu Gln Asn Trp Ser Pro Asp Asn
480                 485                 490

Ala Leu Ile Leu Ser Ala Ala Asn Tyr Pro Thr Trp Ser Ile Thr Val
495                 500                 505                 510

Asn Leu Pro Ala Asn Thr Val Val Gln Tyr Lys Tyr Ile Arg Lys Phe
                515                 520                 525

Asn Gly Gln Val Thr Trp Glu Ser Asp Pro Asn Asn Gln Ile Thr Thr
            530                 535                 540

Pro Ser Gly Gly Ser Phe Thr Gln Asn Asp Val Trp Arg
        545                 550                 555

<210> SEQ ID NO 7
<211> LENGTH: 283
<212> TYPE: PRT
<213> ORGANISM: Bacillus thuringiensis
<220> FEATURE:
<221> NAME/KEY: SIGNAL
<222> LOCATION: (1)..(24)
<220> FEATURE:
<221> NAME/KEY: mat_peptide
<222> LOCATION: (25)..(282)

<400> SEQUENCE: 7

Met Lys Lys Lys Val Leu Ala Leu Ala Ala Ala Ile Thr Leu Val Ala
                -20                 -15                 -10

Pro Leu Gln Ser Val Ala Phe Ala His Glu Asn Asp Gly Gly Ser Lys
             -5                  -1  1                   5

Ile Lys Ile Val His Arg Trp Ser Ala Glu Asp Lys His Lys Glu Gly
         10                  15                  20

Val Asn Ser His Leu Trp Ile Val Asn Arg Ala Ile Asp Ile Met Ser
25                  30                  35                  40

Arg Asn Thr Thr Leu Val Lys Gln Asp Arg Val Ala Gln Leu Asn Glu
                45                  50                  55
```

```
Trp Arg Thr Glu Leu Glu Asn Gly Ile Tyr Ala Ala Asp Tyr Glu Asn
             60                  65                  70

Pro Tyr Tyr Asp Asn Ser Thr Phe Ala Ser His Phe Tyr Asp Pro Asp
             75                  80                  85

Asn Gly Lys Thr Tyr Ile Pro Phe Ala Lys Gln Ala Lys Glu Thr Gly
 90                  95                 100

Ala Lys Tyr Phe Lys Leu Ala Gly Glu Ser Tyr Lys Asn Lys Asp Met
105                 110                 115                 120

Lys Gln Ala Phe Phe Tyr Leu Gly Leu Ser Leu His Tyr Leu Gly Asp
                125                 130                 135

Val Asn Gln Pro Met His Ala Ala Asn Phe Thr Asn Leu Ser Tyr Pro
                140                 145                 150

Gln Gly Phe His Ser Lys Tyr Glu Asn Phe Val Asp Thr Ile Lys Asp
                155                 160                 165

Asn Tyr Lys Val Thr Asp Gly Asn Gly Tyr Trp Asn Trp Lys Gly Thr
170                 175                 180

Asn Pro Glu Asp Trp Ile His Gly Ala Ala Val Val Ala Lys Gln Asp
185                 190                 195                 200

Tyr Ser Gly Ile Val Asn Asp Asn Thr Lys Asp Trp Phe Val Lys Ala
                205                 210                 215

Ala Val Ser Gln Glu Tyr Ala Asp Lys Trp Arg Ala Glu Val Thr Pro
                220                 225                 230

Met Thr Gly Lys Arg Leu Met Asp Ala Gln Arg Val Thr Ala Gly Tyr
                235                 240                 245

Ile Gln Leu Trp Phe Asp Thr Tyr Gly Asp Arg
                250                 255

<210> SEQ ID NO 8
<211> LENGTH: 274
<212> TYPE: PRT
<213> ORGANISM: Thermomyces lanuginosa

<400> SEQUENCE: 8

Glu Val Ser Gln Asp Leu Phe Asn Gln Phe Asn Leu Phe Ala Gln Tyr
  1               5                  10                  15

Ser Ala Ala Ala Tyr Cys Gly Lys Asn Asn Asp Ala Pro Ala Gly Thr
                 20                  25                  30

Asn Ile Thr Cys Thr Gly Asn Ala Cys Pro Glu Val Glu Lys Ala Asp
                 35                  40                  45

Ala Thr Phe Leu Tyr Ser Phe Glu Asp Ser Gly Val Gly Asp Val Thr
 50                  55                  60

Gly Phe Leu Ala Leu Asp Asn Thr Asn Lys Leu Ile Val Leu Ser Phe
 65                  70                  75                  80

Arg Gly Ser Arg Ser Ile Glu Asn Trp Ile Ala Asn Leu Asn Phe Trp
                 85                  90                  95

Leu Lys Lys Ile Asn Asp Ile Cys Ser Gly Cys Arg Gly His Asp Gly
                100                 105                 110

Phe Thr Ser Ser Trp Arg Ser Val Ala Asp Thr Leu Arg Gln Lys Val
                115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
```

-continued

```
                    165                 170                 175
Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195             200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
            245                 250                 255

Ala His Leu Trp Tyr Phe Gln Ala Thr Asp Ala Cys Asn Ala Gly Gly
            260                 265                 270

Phe Ser
```